United States Patent [19]

Doring

[11] 4,402,328

[45] Sep. 6, 1983

[54] CRISTA TERMINALIS ATRIAL ELECTRODE LEAD

[75] Inventor: Carl Doring, Wollstonecraft, Australia

[73] Assignee: Telectronics Pty. Limited, Lane Cove, Australia

[21] Appl. No.: 258,322

[22] Filed: Apr. 28, 1981

[51] Int. Cl.³ .............................................. A61N 1/04
[52] U.S. Cl. .................................. 128/785; 128/786; 128/419 P
[58] Field of Search .............................. 128/784-786, 128/642, 419 P

[56] References Cited

U.S. PATENT DOCUMENTS

| 3,516,412 | 6/1970 | Ackerman | 128/419 P |
| 3,729,008 | 4/1973 | Berkovits | 128/418 |
| 3,902,501 | 9/1975 | Citron et al. | 128/418 |
| 3,939,843 | 2/1976 | Smyth | 128/419 P X |
| 4,057,067 | 11/1977 | Lajos | 128/418 |
| 4,106,512 | 8/1978 | Bisping | 128/418 |
| 4,236,529 | 12/1980 | Little | 128/786 X |

OTHER PUBLICATIONS

Medtronic Clinical Study Report, "Urethane Atrial J. Transvenous Leads," May 1980.
Medtronic's News, Atrial Program Pacing Systems, pp. 6-9.

Primary Examiner—Lee S. Cohen
Attorney, Agent, or Firm—Finnegan, Henderson, Farabow, Garrett & Dunner

[57] ABSTRACT

A J-shaped atrial electrode lead having a pliant tube encasing a spiral wound conductor. A curved, resilient reinforcing member surrounding a portion of the conductor curves the conductor to conform with the shape of the origin of the crista terminalis of the right atrium to position an electrode tip in electrical contact with the junction of the crista terminalis and the superior margin of the right atrial appendage. The lead can be electrically bipolar or unipolar and includes tines adapted for engagement in the right atrial appendage, and an improved proximal portion for connection with a pacemaker circuit module.

69 Claims, 10 Drawing Figures

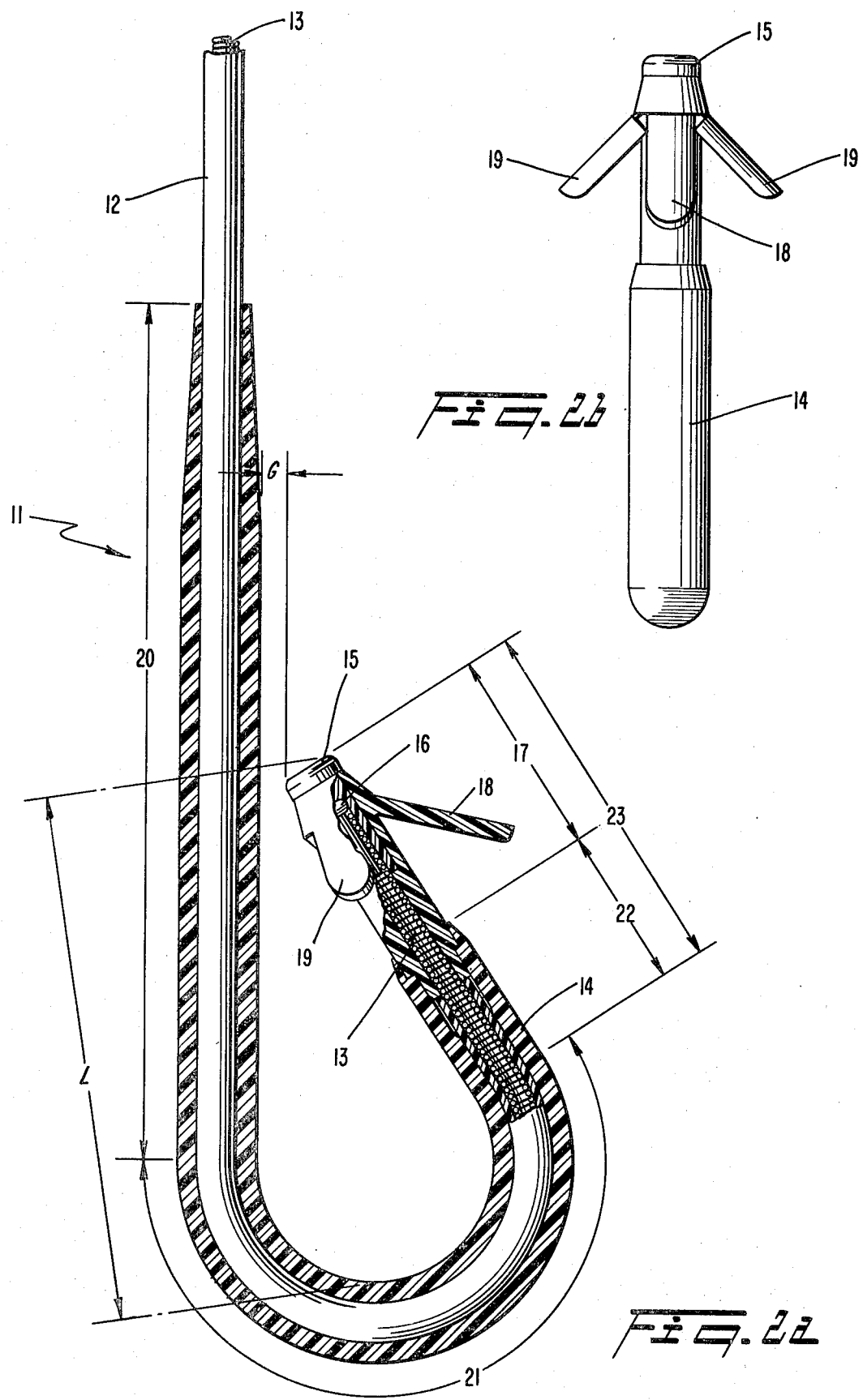

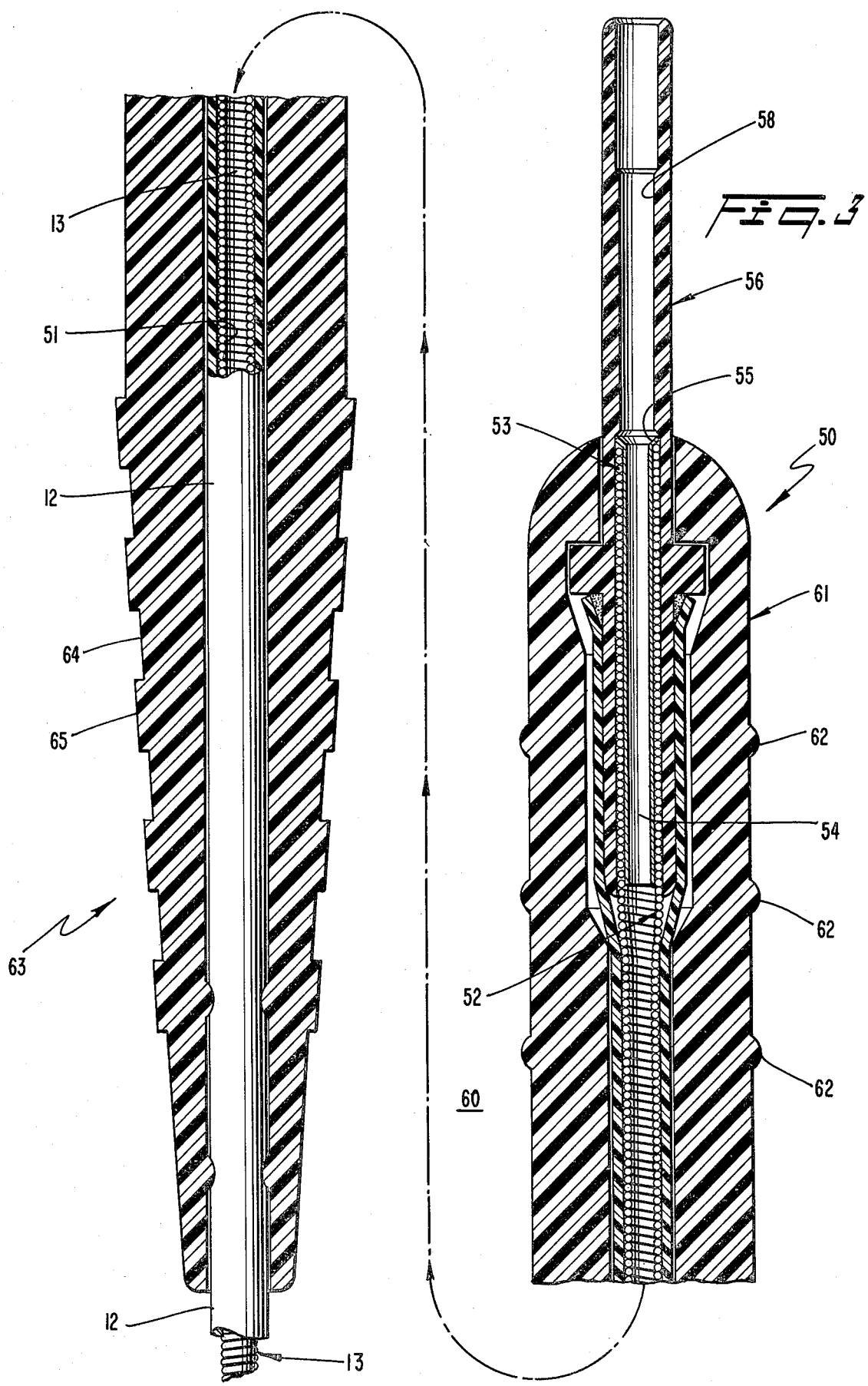

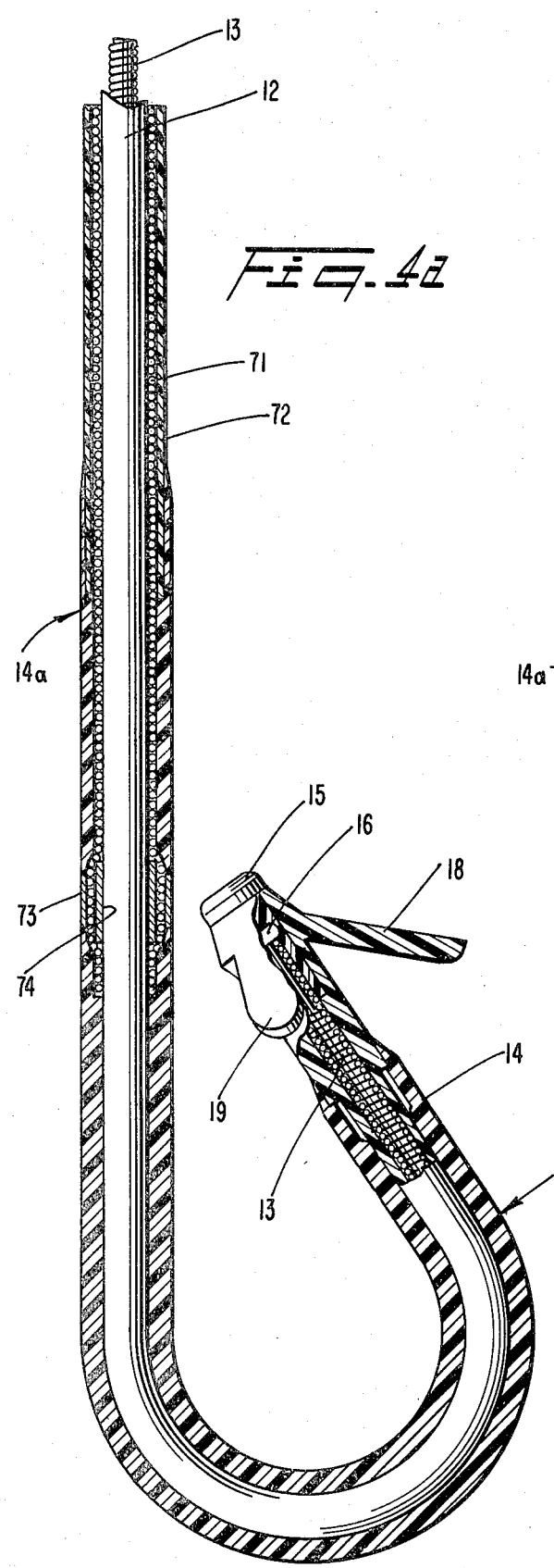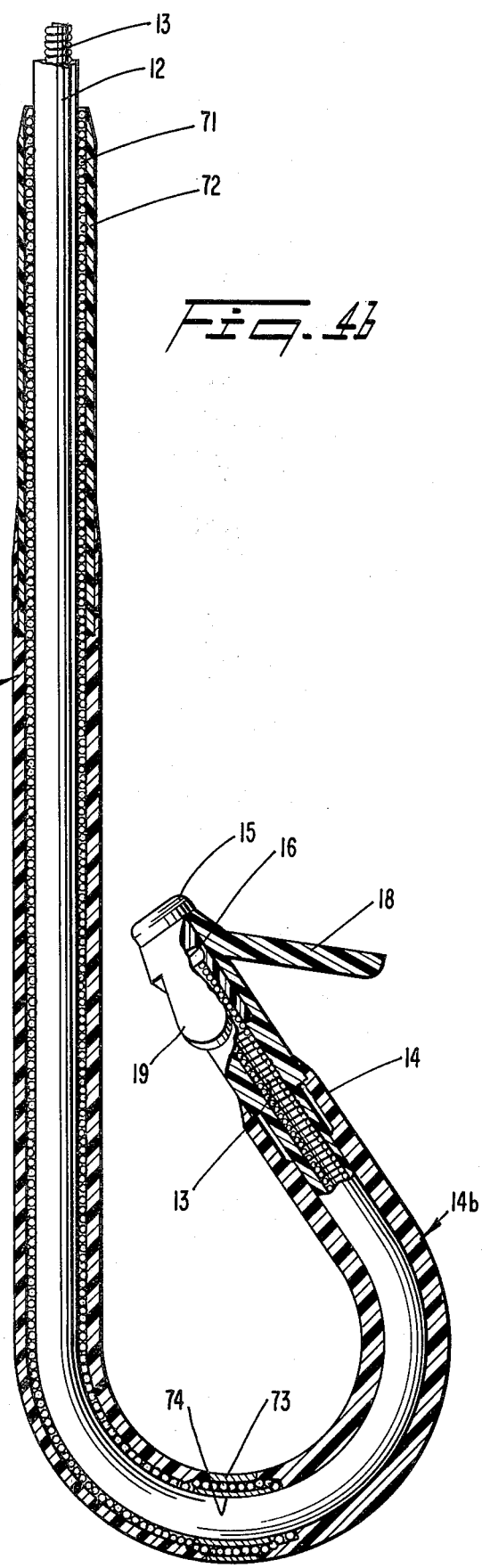

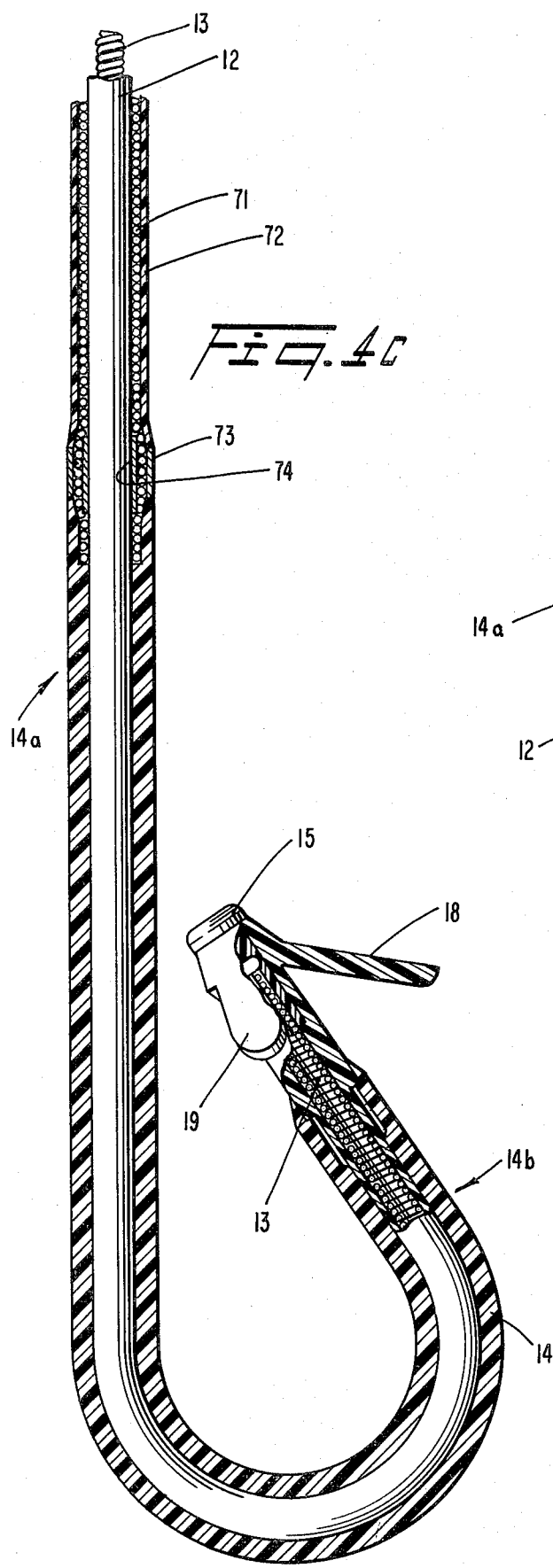
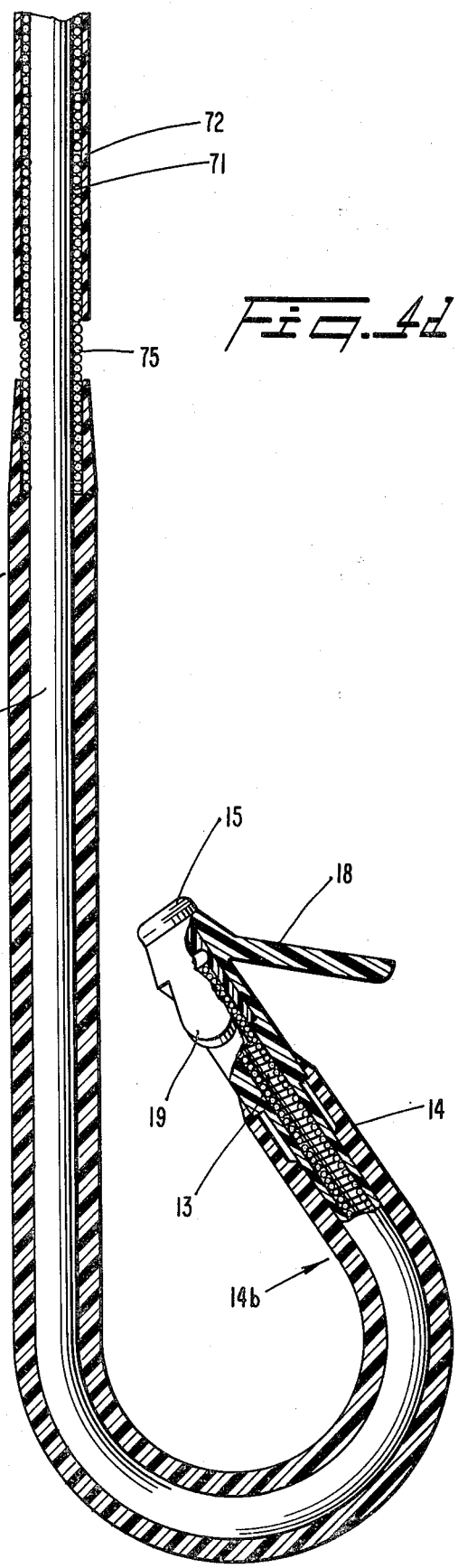

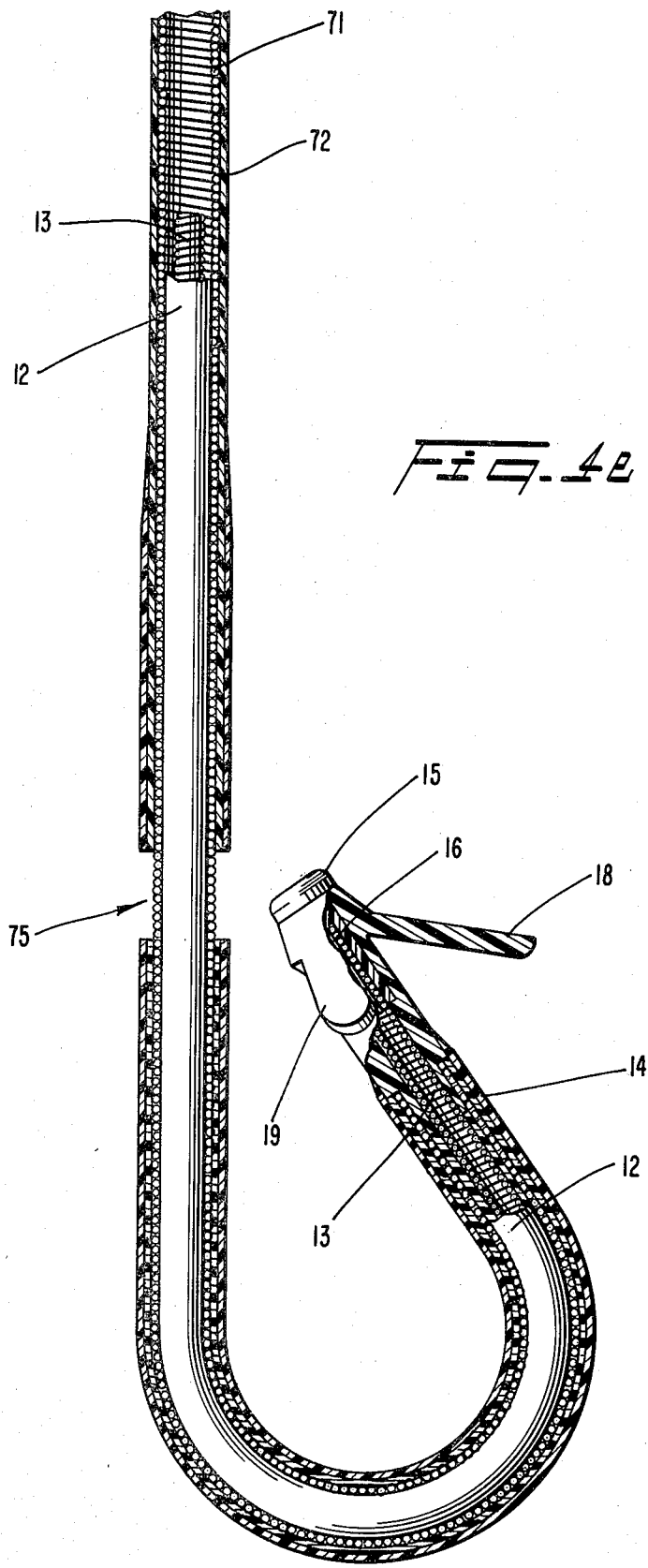

CRISTA TERMINALIS ATRIAL ELECTRODE LEAD

FIELD OF THE INVENTION

This invention relates with particularity to an improved atrial electrode lead for use in combination with a cardiac pacemaker. However, some of the improvements taught in this invention could also be applied to ventricular electrode leads or the dual-chamber atrioventricular electrode leads.

BACKGROUND OF THE INVENTION

Pacemaker manufacturers have been striving to develop satisfactory dual-chambered systems to stimulate the atria and then the ventricles in a sequence that mimics the natural cardiac cycle more closely than do single-chamber systems. Although it has long been known that dual-chamber pacing will give improved physiological cardiac performance and reduced patient morbidity, there have been major obstacles preventing its general use. In particular, there have been problems associated with the atrial leads and the need to have electrode leads in both the right atrium and right ventricle simultaneously.

Until recently, the state-of-the-art in atrial leads was typified by tined Silastic J-shaped leads. (Silastic is a trademark for a silicon rubber composition.) These have typically measured 16 F over folded tines and 10 F over the body of the lead and have to be implanted through a large vein. The unit F indicates French gauge and corresponds to three times the diameter of the lead in millimeters. The Silastic J-shaped leads have been prone to dislodgement and to loss of signal sensing. Their large size and the high friction coefficient of the Silastic coating made the introduction of both ventricular and atrial leads through the same vein cumbersome and difficult.

Recently, several new polyurethane insulated ventricular and atrial leads have been introduced. These leads are thinner and more slippery than their Silastic counterparts because of the use of polyurethane. These properties of polyurethane-insulated leads make it practical to implant two leads through the same vein for dual-chamber pacing. Typically, polyurethane unipolar ventricular leads measure $4\frac{1}{2}$ F over the body and 9 F over the folded tines. One typical polyurethane atrial J lead measures 8 F over the body and 9 F over the folded tines.

The instant invention relates with particularity to an improvement over existing J-shaped atrial lead designs, arising from certain discoveries concerning atrial anatomy. It was discovered that several important features of the right atrial appendage have been incorrectly or inadequately reported in contemporary medical texts. It was after obtaining a clearer understanding of the structure of the right atrial appendage that the construction of the J-shaped atrial electrode of the instant invention was conceived.

A part of this greater understanding, as illustrated in FIG. 1a, is that the crista terminals originates at the junction of the superior vena cava (SVC) 30 and the right atrial appendage (RAA) 33, as a ridge 35 approximately 10–15 mm deep across the superior end of the entrance of the right atrial appendage. Moreover, the junction of the interior of the tent-like superior margin 31 of the right atrial appendage 33 and the intersection of the superior vena cava 30 and the crista terminalis 35 forms a pocket 36 about 10–15 mm deep. However, contemporary medical texts usually depict the superior margin 31 of the right atrial appendage 33 as springing from a point where the superior vena cava 30 opens into the atrium and neglect the ridge and pocket present at the crista terminalis origin. It is this pocket 36 that is a most suitable location for the placing of the electrode tip 15, of a properly constructed J-shaped atrial lead 11, as shown in FIGS. 1 and 2.

The thin walls of the atrium and most of the right atrial appendage 33 are smooth or have only shallow musculae pectinatae 44 (FIG. 1b) closely attached to the walls. This tissue is not easily gripped by tines attached to a J-shaped atrial electrode. However, the musculae pectinatae of the superior portion of the right atrial appendage are partly detached from the walls and form a limited, localized network to which appropriately designed tines can be anchored. This network of musculae pectinatae is deepest and most prolific in region 37 adjacent to the above-mentioned pocket 36, and becomes shallower at region 38 toward the apex 32 of the right atrial appendage 33.

Commonly, it has been attempted to attach J-shaped atrial electrode leads to this apex 32 of the right atrial appendage 33 as shown in phantom in FIG. 1a. These attempts have not proved entirely successful because the shape and size of the right atrial appendage 33 varies considerably in different patients, ranging from a long, sharply peaked triangle to a short, rounded lobe. Such variations suggest that the placements of previously known J-shaped atrial electrode leads have been imprecise and, therefore, not fully reliable. Even when the external shape of the right atrial appendage has a deeply-pointed peak, and thus appears ideal for locating the tip of a conventional J-shaped atrial electrode, it often occurs that internally, the pointed apex is partly sealed-off either naturally or by cardiac surgery, and not open to the admission of the tip of a J-shaped atrial electrode. Also, the apex 32 of the right atrial appendage 33 is relatively unconstrained and executes large and rapid movements during the cardiac cycle, thus making considerable demands on the ability of conventional J-shaped leads placed in the apex to withstand flexural strain and resist accidental dislodgement. In contrast, the pocket 36 formed at the junction of the superior vena cava 30 and the crista terminalis 35 is comparatively consistent in size and location and undergoes relatively small movements during the cardiac cycle.

Conventional atrial electrode leads 40 (FIG. 1a) have been J-shaped as illustrated by U.S. Pat. No. 3,729,008 issued to Dr. Berkovits on Apr. 24, 1973. As stated above, the J-shape of the lead was selected to hold the electrode tip in contact with the apex 32 of the right atrial appendage 33 or against the superior margin of the right atrial appendage 33 close to the apex 32 and far from the superior vena cava 30. To achieve this, the curvilinear section, i.e., the bend in the J-shaped, of the atrial lead was designed to have a natural radius of curvature of approximately one inch or 25 millimeters.

The J-shaped section was fabricated to be relatively stiff and springy when compared to the general body of the atrial electrode lead. However, it could be bent straight for insertion with a stylet but would spring back to its pre-set J-shape when released into the relaxed position.

Oftentimes, the resilient J-shape has been achieved by fitting a J-shaped wire helix, i.e., the conductor of the pacemaker lead, into a relatively thick and stiff Silastic J-shaped molding. This J-shaped molding was connected to the distal end of a Silastic insulating tube covering the general body of the lead.

Polyurethane J-shaped atrial leads commonly have an extra stiffening helix built into the J-shaped portion to provide the necessary spring effect. This is required because polyurethane takes a set when bent and does not perform well as a spring.

OBJECTS AND SUMMARY OF THE INVENTION

It is an object of the present invention to improve the design of atrial electrode leads to enable the anchoring of an electrode tip against the superior margin of the right atrial appendage adjacent to the S.V.C. by curling around the superior end or origin of the crista terminalis.

Another object of this invention is to reduce the diameter of atrial electrode leads to enable the convenient insertion into the heart of ventricular and atrial leads through the same vein.

Another object of this invention is to reinforce atrial electrode leads by providing a curvilinear portion conforming to the shape of the superior end of the crista terminalis and biasing an electrode tip against cardiac tissue at the junction of the S.V.C. and the superior margin of the right atrial appendage.

Yet another object of this invention is to provide an improved atrial electrode lead having a portion with curvature sufficient to cause an electrode tip and a linear portion of the lead to pinch the crista terminalis when the electrode is properly positioned in the heart.

Another object of this invention is to provide an electrode lead that can be easily attached to the musculae pectinatae adjacent to the superior portion of the right atrial appendage.

Additional objects and advantages of the invention will be set forth in part in the description that follows, and in part will be apparent from the description or may be learned from the practice of the invention. The objects and advantages of the invention may be realized and obtained by means of the instrumentalities and combinations particularly pointed out in the appended claims.

To achieve the foregoing objects in accordance with the invention, as embodied and broadly described herein, an atrial electrode lead comprises a pacing conductor having a proximal end and a distal end, a pliant insulating tube surrounding the pacing conductor, an electrode electrically connected to the distal end of the pacing conductor, means for shaping the pacing conductor and the pliant insulating tube to bend around the crista terminalis of the heart to impress the electrode into substantial electrical contact with the superior margin of the right atrial appendage, and means at the proximal end adaped to connect the electrode lead to a cardiac pacemaker circuit module.

BRIEF DESCRIPTION OF THE DRAWINGS

The manner in which the apparatus of the present invention is constructed and its mode of operation can best be understood in the light of the following detailed description, together with the accompanying drawings in which:

FIG. 2a is a cross-sectional view of the distal portion of the J-shaped atrial electrode lead of the instant invention;

FIG. 2b is a view of the distal end of the J-shaped atrial electrode lead of FIG. 2a.

FIG. 3 is a cross-sectional view of the proximal pacemaker-connecting coupling member assembly of the J-shaped atrial electrode lead of the instant invention; and FIGS. 4a-4e illustrate bipolar embodiments of the instant invention.

DETAILED DESCRIPTION OF THE PREFERRED EMBODIMENT

The first and second preferred embodiments of the instant invention, described below, incorporate many novel improvements to atrial leads. For example, one improvement concerns the achievement of a shape and size of the J-shaped distal portion of the atrial lead to promote the placement of the electrode tip in the desired location in the atrium. The design of the J-shaped portion also promotes the stable contact of the electrode tip against the atrial tissue in that region. This improvement is further illustrated in two preferred embodiments, the first embodiment optimizing the stability of the electrode contact after implant and the second embodiment facilitating the placement of the electrode during implant.

Another improvement concerns a preferred means of constructing the lead to achieve the desired J-shape. While yet another feature concerns the use of tines designed specifically to enhance entrapment in the trabeculated musculae pectinatae found in the desired location in the atrium.

Also, a preferred means of constructing the proximal connector to obtain several benefits, particularly a reduction in the overall diameter of the central and distal portions of the lead, is incorporated into the instant invention.

The two preferred embodiments described below incorporate all of these features. However, other embodiments could be made incorporating only one, two, or three of the improvements whle remaining substantially within the scope and spirit of this invention.

Figure 1B:
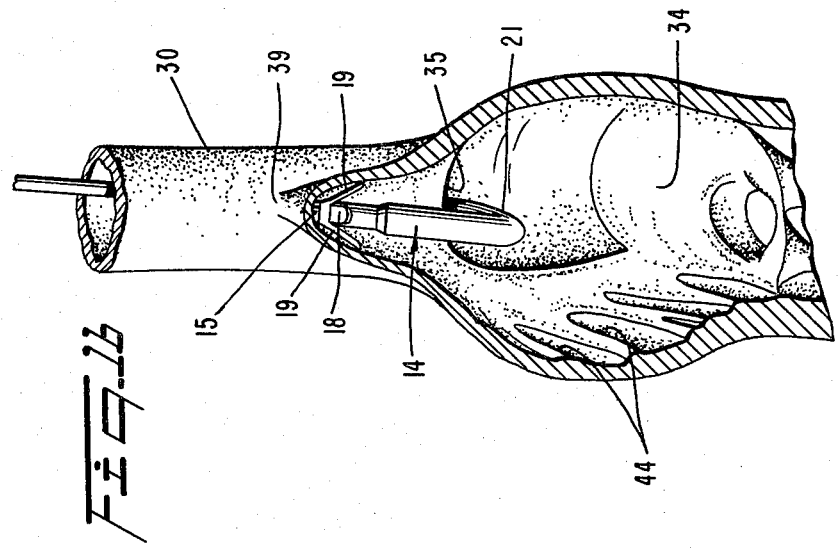
FIG. 1b is a cross section of FIG. 1a taken along the lines 1b—1b.
Figure 1A:
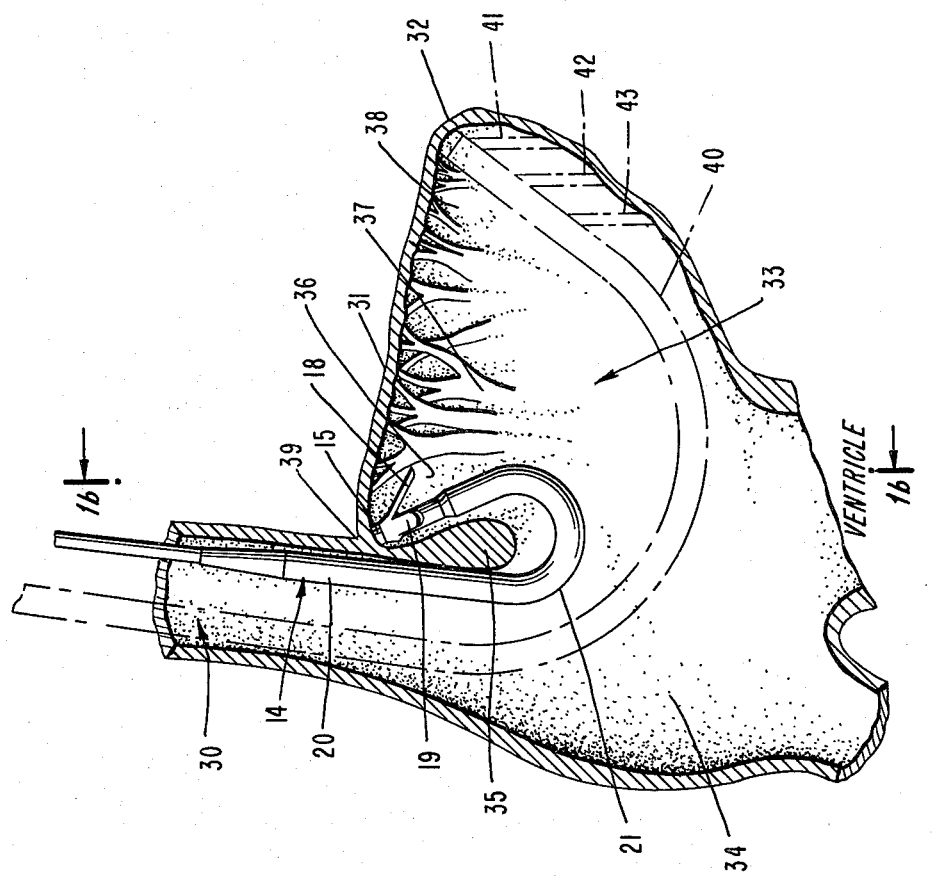
FIG. 1a is a schematic illustration in cross section of the J-shaped atrial electrode lead of the instant invention properly positioned within a human heart.

Referring to FIG. 2a, a reinforced portion of the J-shaped atrial electrode lead 11 of the instant invention is illustrated in cross section. The lead 11 includes a pliant insulating tube 12 covering a pacing conductor 13. As embodied herein, the pliant tube 12 is a polyurethane sheath surrounding a spirally wound pacing conductor 13. Means are provided for shaping the pliant tube 12, and the conductor 13 therein, to bend the pliant tube 12 and the conductor 13 around the crista terminalis 35 of the heart and to impress a distal electrode 15 into substantial electrical contact with the superior margin 31 of the right atrial appendage 33 of the heart adjacent to the superior vena cava 30, as shown in FIGS. 1a and 1b. As embodied herein, the primary shaping means comprises a resilient, molded Silastic J-shaped molding 14 surrounding the pliant tube 12 and the conductor 13, and holding them in a substantial J-shape. As embodied herein, the conductor 13 is also pre-formed to a J-shape and its own resilience provides a secondary shaping means of significantly less effect than the primary shaping means 14 as the conductor 13 is chosen for high flexibility and low flexural stress, rather than for high resilient stiffness.

As embodied herein, the J-shaped molding 14 includes a long straight proximal leg 20, a curvilinear or arcuate portion 21, and a short straight distal leg 22. The curvilinear portion extends over more than 180° so that the leg 22 tends to converge towards leg 20. A separate Silastic molding 17, incorporating tines 18 and 19 (FIG. 2b), is bonded to the end of leg 22 and effectively extends leg 22 up to the distal electrode 15, which is close to leg 20.

As shown in FIGS. 1a, 1b, and 2a, the J-shaped lead 11 as embodied herein is designed such that the proximal leg 20 resides within the superior vena cava (S.V.C.) 30. The arcuate portion 21, in turn, curves closely around the bulbous ridge of the origin of the crista terminalis 35. The distal leg 23 (incorporating sections 17 and 22) extends into the pocket 36 formed in the right atrial appendage (R.A.A.) 33 at the junction between the S.V.C. 30 and the tent-like superior margin 31 of the R.A.A. 33. The distal electrode 15 will be held in contact with the cardiac tissue in the vicinity of the junction 39 between the R.A.A. 33 and S.V.C. 30. To achieve this the dimensions of the lead are chosen to suit the relevant atrial anatomy, as is explained below, with reference to FIGS. 1a, 1b, and 2a.

The radius of curvature R of the curvilinear portion 21 of the Silastic reinforcing member is preferably in the range of 3 mm to 8 mm, and ideally approximately 5 mm, measured to the innermost surface of the curvilinear portion 21, not measured to the pitch circle radius at the center of the conductor 13. This range of radii is chosen so that the J-shaped portion of the atrial electrode lead will fit closely around the bulbous ridge of the crista terminalis 35 without tightly binding and causing the electrode tip 15 to be held away from the active tissue.

In the preferred embodiment, the distal leg 23 of the J-shaped electrode lead 11 has a length such that the distance L is in the range of 15 mm to 28 mm and is preferably between 20 mm and 25 mm. This distance L is measured from the tip of the distal electrode 15 to the furthest portion of the inner curved face of the curvilinear portion 21. This range of length ensures that the electrode tip 15 will contact the superior margin 31 of the right atrial appendage 33 when the J-shaped atrial electrode lead is positioned properly in the atrium. If the leg 23 is too short, the curvilinear portion 21 rests against the crista terminalis 35 in a manner that prevents the electrode tip 15 from firmly contacting the superior margin 31 of the right atrial appendage 33. If the leg 23 is too long, the control of gap G between the electrode tip 15 and the leg 20 will be impaired, making the final placement of the electrode tip 15 more difficult and reducing the contact force that can be generated between electrode tip 15 and the adjacent tissue.

In the preferred embodiment shown in FIG. 2a, the length and angle of the distal leg 23 is chosen such that the gap between the distal electrode tip 15 and the proximal leg 20 is within the range of zero to 5 mm, or such that the electrode 15 overlaps the proximal leg 20 by zero to 5 mm. Preferably the gap G is about zero to 1 mm. This small gap or small overlap ensures that when the lead 11 is correctly placed in the atrium the crista terminalis tissue is lightly pinched between the electrode 15 and the leg 20, thereby enhancing the stability of the lead and the intimate contact of the electrode 15 against the cardiac tissue. If the gap G is larger than 5 mm the pinch effect is reduced or lost. If the overlap is made greater than 5 mm there is an increasing tendency for the J-shaped portion to twist out of shape and out of position.

During implant, the J-shaped section 14 of the atrial electrode lead of the instant invention is temporarily straightened by fully inserting a stylet into the lumen of the conductor 13, as in the prior art. The lead and stylet are passed down through the veins and the superior vena cava 30 until the J-shaped portion 14 of the atrial electrode lead is present in the atrium. The following steps are then taken to insure correct final placement of the electrode tip 15 against the superior margin 31 of the right atrial appendage 33 adjacent to the junction of the crista terminalis 35 and the superior vena cava 30:

(i) The stylet is retracted sufficiently to allow the J-shaped section 14 to regain its relaxed or J-shape partly, until gap G is temporarily in the range of 5 to 15 mm, preferably 10 mm.

(ii) The distal leg 23 and the electrode tip 15 are positioned to point towards, not away from, the right atrial appendage 33; and (iii) The leg 20 lies lightly against the side of the superior vena cava 30 opening closest to the right atrial appendage 33, an orientation achieved by appropriately pre-forming the shape of the stylet.

When these three conditions are achieved, as seen on a fluoroscope, a light pull on the lead pulls the electrode tip 15 and the distal leg 23 of the reinforcing member 14 into the pocket 36 formed at the junction of the superior vena cava 30 and the crista terminalis 35. When the stylet is fully withdrawn, the gap G tends to close further until the crista terminalis 35 is lightly pinched between the electrode tip 15 and the leg 20.

In an alternative embodiment based upon the structure shown in FIG. 2a, the distal leg 23 is made more nearly parallel to the leg 20 by reducing the angle of the curvilinear portion 21 such that the lead 11 naturally assumes a gap G in the range of 5 mm to 15 mm and preferably a gap G of 10 mm. This aids the positioning of the electrode 15 within the pocket 36 because the correct gap for placement is achieved without the need to control precisely the degree to which the stylet is partially withdrawn. This increased natural gap G reduces or eliminates the abovementioned pinching effect, and thus relies on the entrapment of the tines 18, 19 in the deeply trabeculated and comparatively immobile pocket 36 to give enhanced stability of position of the electrode tip relative to the conventional J-shaped lead placed in the R.A.A. apex 32.

If gap G is made larger than 15 mm there will be an increasing risk that the tip 15 will miss the desired pocket 36 and will instead lodge in the more mobile, more shallowly trabeculated zone closer to the R.A.A. apex 32.

The length of the proximal leg 20 is not critical, but preferably leg 20 should extend up the S.V.C. 30 to at least the level of the distance electrode 15, so that contact forces between the S.V.C. and leg 20 (generated in reaction to the pinching force and the contact forces at the electrode tip 15) will be well spread and stable. This also insures that the bending moments generated in the J-shaped portion will be absorbed within the stiff J-shaped molding 14 and will not cause sharp bending of the unstiffened conductor 13 and sheath 12 outside the J-shaped molding. In the preferred embodiment the leg 20 is about 35 mm long.

Conventionally the prior art J-shaped atrial leads have used Silastic tubing to cover the conductor, Silastic tines to anchor the tip, and a Silastic J-shaped molding to shape the distal end of the lead and to maintain the J-shape and the contact force at the electrode tip even after years of implant. The ability of the highly resilient Silastic to maintain its shape and spring function in the long term is well proven by the prior art leads.

Recently, atrial J-leads have been introduced using polyurethane as the external sheathing tube over the conductor in both the straight and J-shaped regions. As stated above, polyurethane is not as resilient or "springy" as Silastic, but creeps under load and cannot be relied on to maintain the J-shape and the required electrode tip contact force. Consequently, the prior-art polyurethane J-shaped leads have been provided with metallic J-shaped spring elements, either by fitting an additional J-shaped stiffening helix around the conductor helix 13, or by increasing the stiffness of the conductor helix 13 itself. Both of these methods have disadvantages. If the stiffness of the conductor helix 13 is increased considerably above normal to provide sufficient spring force to maintain effective tip contact, the risk of a fatigue fracture is also increased. Although an extra stiffening helix, if carefully designed, can sustain acceptable stresses, it is usually terminated just proximal to the J-shaped portion to minimize the diameter of the lead body. That discontinuity produces awkward construction details, and the sudden change in stiffness tends to concentrate flexural strain at that point and encourage fatigue failure of the conductor helix 13.

The preferred embodiment of the instant invention uses a novel composite construction with thin slippery polyurethane tubing insulating the conductor helix 13, and a resilient J-shaped Silastic molding 14 providing the shaping means and the long-term spring action. This composite construction gives the following and other advantages over the prior-art leads:

(a) It enables the optimum material properties to be chosen for both the insulating tube and J-molding.

(b) The Silastic J-shaped molding body may be manufactured by a relatively simple and well-proven process to give good control of shape and dimensions, and to permit the cross section of the molding to be varied along its length distributing optimally flexural stiffness. In particular the proximal end of the J-molding can be gently tapered to provide smooth transition (in size and stiffness) between the J-shaped portion and the general body of the lead.

(c) The conductor helix is not required to act as a stiffening spring, and can be designed to have low flexural stiffness, low flexural stress, and a long fatigue life.

This composite construction lead with polyurethane tubing and distal Silastic J-molding has not previously been used and represents an improvement in the art.

Although Silastic moldings have been used as part of the proximal connector on polyurethane-sheathed leads to provide a resilient fluid-tight seal when inserted into the rigid connector socket of some pulse generators, this represents a completely different application of composite Silastic/polyurethane lead construction and is quite outside the concept of the instant invention.

The trabeculae of the right ventricle are generally long and profuse, providing many sites in which tined leads can be securely lodged—and thus the length of tines on ventricular leads is not a critical design criterion. In contrast, the musculae pectinatae (equivalent to the trabeculae of the ventricle) of the atrium offer relatively few sites for engagement of tines, and so the tines on an atrial lead must be designed specifically to suit the intended sites in order to give the maximum likelihood of secure anchoring of the lead tip.

The tines are intended to fold in a proximal direction against the body of the lead while passing through a narrow gap between "trabeculae", then spring open once past the narrow portion to engage the distal face of the "trabeculae" and inhibit any tendency for the lead to slide back out of the lodgement site. If the tines are too long they will not spring out but will remain ineffectually folded within the narrow gap. If the tines are too short the tip is able to slide out of contact with active tissue before the tines have gripped the trabeculae.

The depth to which the lead has to be inserted into a trabeculated pocket before the tines spring out to engage the trabeculae is called the "engagement depth," and is determined by the length from the forward face of the distal electrode to the rear or proximal tip of the folded tines. The overall depth of the "trabeculated" musculae pectinatae at the superior margin of the right atrial appendage typically varies from about 10 to 15 mm at the pocket 36 adjacent to the S.V.C. 30 (where the instant invention is intended to be placed) to about 5 mm or less at the apex 32 of the R.A.A. 33 (where conventional J-leads 40 are placed). Allowing for the thickness of musculae pectinatae, the corresponding tine engagement depth varies generally from 6 to 12 mm near the S.V.C. down to 2 to 4 mm at the apex (see FIG. 1a).

Typical tined Silastic J-leads, as shown in phantom in FIG. 1a, have three rows of three long tines, 41, 42 and 43, with engagement depths of about 19, 24 and 29 mm, respectively. Typically, recent polyurethane J-shaped leads have one row of three equal-length tines, giving an engagement length of about 9 or 10 mm. Such a single row of tines does not suit the full range of engagement depths found in the R.A.A. 33, indeed it is difficult to have any uniform-length tine array that would cope with the full range of anatomical variations. Consequently, the preferred embodiments of the instant invention are provided with tines of unequal length to improve the chance for satisfactory engagement of at least one of the tines with the heart tissues.

The engagement lengths chosen are approximately 6 mm for the two "side" tines 19 (FIG. 2b) and approximately 8 mm for the central "rear" tine 18 (FIG. 2b), so that at least two and frequently three tines will be engaged. The free movement of such a tined lead will usually be less than 2 mm. Other designs with one or more short tines in the range 4–6 mm and one or more long tines in the range 8–12 mm are also suitable for the half 37 of the superior margin of the R.A.A. 33 closest to the S.V.C. 30 where the most prolific atrial "trabeculation" occurs.

The tines of the preferred embodiment are made of Silastic, which offers some advantages over polyurethane tines in the atrium. Silastic tines are more resilient and, thus, more able to cope with the large variations between different hearts, and with the large degree of swelling and contraction that occurs in the atrium during each cardiac cycle. Silastic is also softer than polyurethane and less likely to puncture or abrade the extremely thin walls found in many parts of the atrium.

There is a constant striving within the pacemaker art to reduce the diameter of electrode leads and an additional feature of the instant invention is a means for achieving a significant reduction in the diameter of the conductor helix 13, and hence a reduction in the outside diameter of the conductor sheath 12 and the distal tip. Several other improvements in the construction of the proximal connector are also taught. The improvements are described in relation to the preferred embodiment of atrial J-shaped leads shown in FIG. 2a, but could be applied equally well to other atrial, ventricular or dual-chamber leads.

For many years the typical electrode lead conductor had consisted of a single wire of about 0.25 mm diameter formed into a helix with approximately a 1 mm outside diameter and 0.5 mm inside diameter. The lumen of such a helix accepts the insertion of a stylet wire with typically a 0.35 to 0.40 mm diameter to stiffen the lead for easier implantation.

Recently it has become common to use a multi-filar (multi-wire) helix with, for example, three strands of relatively fine wire of about 0.125 mm diameter, wound in parallel. The finer wire gives the multi-filar helix greater flexibility, lower flexural stress, and longer fatigue life than the typical single-wire helix. The finer wire should have permitted the helix outside diameter to be reduced to about 0.75 mm while still retaining an inside diameter of 0.5 mm, but to date this has not been achieved due to constraints imposed by the proximal connector construction.

Usually the conductor helix is connected to a cardiac pacemaker circuit module via a rigid tubular proximal pin which is permanently fixed to the proximal end of the helix. During manufacture the helix is inserted into a large aperture at one end of the proximal pin, and that end of the pin is swaged or crimped onto the helix to provide a permanent mechanical and electrical joint A smaller axial through-hole in the remainder of the proximal pin lines up with the lumen of the helix and permits stylet entry.

The single-wire helix with a 0.25 mm wire is strong enough to withstand the swaging forces without collapsing inwards. However, the finer-wire, multi-filar helices must be suported by a short, thin-walled metal reinforcing tube placed inside the proximal end of the helix in the vicinity of the swaged joint, to prevent the helix from collapsing inwards thereby resulting in a weak joint as well as restricting stylet entry. The reinforcing tube typically has a bore of about 0.5 mm to pass the stylet, and a wall thickness of about 0.1 mm to 0.15 mm, giving the tube an outside diameter of about 0.7 to 0.8 mm.

Consequently, the prior art, fine-wire helices have had an inside diameter of about 0.75 mm and an outside diameter of about 1.0 mm throughout their entire length, just to accommodate the proximal reinforcing tube. Thus, the use of fine-wire helices has not significantly reduced the overall lead diameter.

The fine-wire helix 13 of the instant invention, shown in FIG. 3, is stepped, i.e., has two zones of different diameters. The main length 51 of the helix is made to have an inside diameter just large enough to accept the stylet. However, at its proximal end 53, the inside diameter of the helix 13 is increased to a sufficient diameter and for sufficient length to accept insertion of a proximal reinforcing tube 54. Typically, the proximal end of this helix has an inside diameter of about 0.75 mm over a 10 mm length, to match the outside dimensions of the reinforcing tube. Beyond this the helix 13 has a short tapered transitional zone 52, leading to the main length 51 of the helix having uniform size of about 0.5 mm inside diameter and 0.75 mm outside diameter, i.e., about 0.25 mm or ¾ F smaller than the prior art helices. This permits the outside diameter of the sheath 12 over the body of the lead, the shank of the distal electrode tip, and the sheath and/or fixation device (e.g., tines) at the distal tip, to be reduced by about ¾ F, compared with equivalent prior art leads. Considering that typical prior art polyurethane sheathed ventricular leads have a body diameter of 4½ F to 5 F, this represents a significant reduction in the diameter of stylettable leads.

The stepped two-diameter helix of the instant invention can be made by at least two commercially viable methods:
(a) Winding the helix on a specially made two-diameter forming mandrel, or
(b) Winding the helix with a uniform diameter over its entire length, expanding a short zone at the proximal end by forcing an appropriately over-size needle into the lumen, then removing the needle and letting the helix spring back to the desired proximal diameter.

A secondary benefit of the stepped two-diameter helix is that a non-flared reinforcing tube (as is commonly used) is prevented from drifting out-of-position down the helix during assembly. In fact, the preferred reinforcing tube of the instant invention includes a flared portion 55 at its proximal end to prevent such drift, and to present to the stylet a smooth bellmouth lead-in without risk of obstruction by an irregularly-cut helix end.

The proximal connector 50 of the instant invention is enclosed in a tubular Silastic molding 60, as is typical of prior art Silastic-sheathed and polyurethane-sheathed leads. Typically, the proximal molding has a proximal parallel portion 61 with sealing rings 62 designed to be inserted into, and tightly sealed against the connector socket of a cardiac pacemaker circuit module.

Typically, the distal portion 63 of the proximal molding is in the form of a tapered tail which protrudes from the pacemaker socket and prevents the sharp bending of the conductor at the point of entry into the socket. Whereas the prior art proximal connector moldings had a smooth taper surface, the proximal molding of the instant invention has a series of circumferential grooves 64 and ridges 65 on the tapered portion 63, which afford a good grip to a surgeon wearing wet gloves when trying to insert or remove the proximal connector into or from the pacemaker socket. The grooves 64 and ridges 65 enable the direct and secure transfer of force from the surgeon's hand into the molding 60 necessary to overcome the friction at the tight-fitting interface between the molding 60 and the pacemaker socket. This minimizes the risk that the surgeon's grip on the taper may slip, causing him to push on and buckle the helical conductor, thus, creating a potential fracture site, or to pull on the conductor and strain the helix or the internal swaged joint. The grip rings are progressively reduced in diameter towards the distal end to retain the general form and strain-relief function of the taper section.

The above-described embodiments of the instant invention are of the unipolar type, with one distal electrode (used for both sensing and stimulating cardiac muscle activity), one conductor, and one proximal connector. Unipolar leads are widely used for single-chamber pacing, and are normally connected to a unipolar pulse generator (pacemaker) with a metallic case acting as the indifferent electrode, also called the "reference," "return," or "ground" electrode. Some dual-chamber pacemakers use two unipolar leads (i.e., one in the right ventricle and one in the right atrium), again with the pacemaker circuit module case acting as the indifferent electrode for both sensing and pacing functions.

Although unipolar systems are simple and are generally preferred for conventional single-chamber ventricular pacing, they sometimes cause problems due to the inclusion of non-cardiac nerves and muscles in the electrical "return" path between the distal electrode and the pacemaker case. For example, the pacing pulse to the heart might also stimulate skeletal muscle near the indifferent case, or electrical signals from skeletal muscle may be detected by the pacemaker and wrongly interpreted as being cardiac muscle signals. This latter problem is particularly relevant to atrial pacing or dual chamber pacing, as the atrial muscle signals tend to be small and easily masked by extraneous signals.

Consequently, it is sometimes preferable to use bipolar leads carrying both the sense/stimulate electrode and the indifferent electrode relatively close together at the distal end of the lead and connected proximally to a bipolar pacemaker via two electrically independent conductors. Commonly, the sense/stimulate electrode is smaller and is placed at the extreme distal end of the lead. The indifferent electrode is in the form of a cylindrical band several times larger in area than the distal electrode, and positioned about 15 to 30 mm proximally along the lead from the distal electrode. Thus, both electrodes will be entirely within the atrium or ventricle, as appropriate, and will be relatively unaffected by the more remote skeletal muscles.

Generally, the bipolar pacemaker has an electrically inactive case and the indifferent electrode on the bipolar lead is used in both sensing and stimulating modes. However, in some applications the lead's indifferent electrode is used for sensing only, and the pacemaker case acts as the indifferent electrode when delivering the pacing pulse. For example, a dual chamber pacemaker could use a bipolar lead in the atrium to sense the normal atrial contraction, then use a unipolar ventricular lead and indifferent case to deliver a synchronized pacing pulse to the ventricle.

The following teaches a number of preferred bipolar embodiments of the instant invention crista terminalis J-shaped lead for use in dual chamber pacing or atrial-only pacing systems, operating in (1) sense-only, (2) pace-only, or (3) sense-and-pace modes. Three of the preferred bipolar versions are distinguished by the choice of position of the indifferent electrode relative to the J-shaped section and the distal electrode. This gives them certain performance characteristics which will make the embodiments better for certain applications. Further preferred embodiments, illustrating other methods of construction, are also discussed. Their common features are described first, with reference to FIG. 4a, then their particular features and differences are described later.

All of the illustrated bipolar embodiments of the instant invention have a first (distal) electrode 15, first conductor 13, first conductor insulating tube 12, resilient J-shaping means 14, and tines 18 and 19, all being generally similar to those of the unipolar embodiments already described. In addition, the bipolar embodiments have a second conductor 71 insulated from the first conductor by the sheath 12 and covered by a second pliant insulating tube 72. The second conductor 71 is connected to a second proximal connector (not shown). In the embodiments of FIGS. 4a, 4b, and 4c, the second conductor 71 is attached to a metallic ring 73 forming the second electrode. In the embodiments of FIGS. 4d and 4e a portion 75 of the second conductor 71 is exposed to act as the second electrode. The embodiments of FIGS. 4d and 4e offer a simpler construction but are generally used for sense-only applications to avoid carrying the substantial pacing currents through the helix/blood interface with a consequent increased risk of helix corrosion.

All the bipolar embodiments of the instant invention crista terminalis atrial J-lead have advantages over the prior art bipolar J-leads, similar to the advantages described previously for the equivalent unipolar embodiments. In addition, the bipolar embodiments of the instant invention have the advantage of allowing much more precise and stable positioning of the indifferent electrode relative to the atrium/S.V.C., than do the prior art bipolar J-shaped leads which are placed in a less well-defined location in the highly variable and mobile apex 32 of the R.A.A. 33. Thus, the position of the indifferent electrode of the instant invention can be chosen with unusual precision to best suit the pacing and/or sensing characteristics of the pacemaker circuitry module and the patient's cardiac conduction system, and once implanted will be more physically stable and hence more consistent in electrical performance than prior art leads.

In the embodiment of FIG. 4(a), the second electrode 73 is positioned within the straight proximal leg 20 of the J-shaped molding 14, such that the first electrode 15 and the second electrode 73 are at substantially equal distances from the center of curvature of the arcuate portion 21, i.e., such that electrodes 15 and 73 are in close opposition to each other. This embodiment has (and all subsequently described bipolar embodiments have) a geometry similar to that of the unipolar embodiment described above. When correctly placed in the atrium, as shown in FIG. 1a, i.e., with the distal electrode tip 15 in the R.A.A. "pocket" 36 and with the indifferent electrode 73 in the S.V.C. 30, the two electrodes will lightly pinch or press against the intervening tissue. This includes active, excitable myocardial tissue at the junction of the crista terminalis 35 origin and the superior margin 31 of the R.A.A. 33. This location is close to the sinoatrial node which is the natural center for the initiation of the cardiac cycle. Thus, this is physiologically a highly favorable area for sensing and stimulating atrial muscle activity.

Due to the close spacing and intimate contact of the two electrodes they should, in the sensing mode where voltage differences between the two electrodes are detected, be particularly sensitive to atrial signals originating close to them, and relatively insensitive to signals coming from more remote ventricular or skeletal muscles.

FIG. 4(a) shows the electrode 73 connected to the conductor 71 by means of trapping the conductor 71 between the electrode 73 and a short metal internal tube 74. Other connection means known in the prior art could be equally well used. FIG. 4(a) also shows the J-shaped molding 14 as being formed in two sections 14(a) and 14(b), respectively, proximal to and distal to the indifferent electrode 73. Section 14(a) does not need to be as resilient as section 14(b), and could be made of the same pliant material as tube 72 or could be eliminated by continuing tube 72 to meet electrode 73.

Other variations within the spirit of the embodiment illustrated in FIG. 4a would be to further enhance intimate tissue contact of the indifferent electrode by making the electrode 73 protrude beyond the outside diameter of the leg 20 or by shaping the leg 20 with a bend at the level of the electrode 73 convex with respect to the electrode 15, such that the electrode 73 tends to be the part of leg 20 to first contact with the S.V.C. wall.

In the embodiment of FIG. 4b, the indifferent electrode 73 is positioned within or near the arcuate portion 21. This embodiment places the indifferent electrode 73 closer to the main body of blood in the atrial chamber. This configuration is advantageous for certain patient conditions and certain pacemaker types.

In the embodiment of FIG. 4c, the indifferent electrode 73 is placed more proximally than the level of the distal electrode 15. In this example the electrode 73 is at the proximal end of J-shaped molding 14. The molding 14 is formed in one piece. This configuration places the indifferent electrode 73 well into the S.V.C. 30, in a zone of minimal extraneous muscle signals. The indifferent electrode 73 could be positioned even further proximally into the S.V.C. 30, but preferably should not be more than 50 mm removed from the level of the distal electrode 15 to avoid returning to an excessive level of extraneous muscle signals.

In the embodiment of FIG. 4d, the separate electrode ring is eliminated and instead a length 75 of the second conductor 71 is exposed to perform the function of the indifferent electrode. This embodiment is otherwise similar to the embodiment of FIG. 4c. The same exposed-helix electrode form could be used in other described embodiments and electrode positions. This construction is simpler for manufacture and is applicable for applications where only sensing is required.

In the embodiment of FIG. 4e, the Silastic J-shaping means is eliminated and its function is performed by using a relatively stiff J-shaped second conductor 71, sheathed in a relatively thin pliant insulating tube 72. This shaping means could be used in unipolar versions of the instant invention, but is particularly suited to bipolar types which must have a second conductor anyway. In the embodiment shown in FIG. 4e, the indifferent electrode is formed by exposing a section 75 of the second conductor 71, level with the distal electrode 15. The electrode 15 is also positioned in the pocket 36 as previously explained.

The instant invention incorporates a number of improvements described above, which can be classified briefly as:

(a) Crista terminalis J-shaped lead geometry, in "pinch" and "non-pinch" versions, and in unipolar and bipolar constructions.

(b) Composite construction with a molded resilient (e.g., Silastic) J-shaping means and a pliant (e.g., polyurethane) insulating tube.

(c) Atrial tines of specific unequal sizes to enhance anchoring in the superior margin 31 of the R.A.A. 33.

(d) Improved proximal connector design giving several advantages, and in particular the use of a stepped-diameter helix to reduce critical lead diameters.

It will be obvious to one practiced in the art that the above features need not all be used simultaneously within the one lead but that significant advantage can be gained from the teachings of the instant invention even if only one, two, or three of the features are adopted in construction of a lead. It will also be obvious that although most of the teachings are particularly relevant to leads used in the right atrium for single-chamber pacing, dual chamber pacing, diagnostic investigation, etc., some of the teachings, and particularly the teachings relating to the improved proximal connector design, are equally applicable to leads used in the right ventricle.

What is claimed is:

1. An atrial electrode lead for connection to a cardiac pacemaker circuit module comprising:
   a first conductor having a proximal end and a distal end;
   a first pliant insulating tube surrounding said first conductor;
   a first coupling member electrically connected to said proximal end of said first conductor, for connecting said first conductor to said cardiac pacemaker circuit module;
   a distal electrode tip electrically connected to said distal end of said first conductor; and
   means for shaping said first conductor to bend around the crista terminalis of the heart to place said distal electrode tip into substantial electrical contact with cardiac tissue at the junction of the superior margin of the right atrial appendage and the origin of the crista terminalis once said atrial electrode lead is inserted into the right atrium of a human heart.

2. An atrial electrode lead according to claim 1 wherein said shaping means further reinforces said first conductor proximally to said distal electrode tip to shape said first conductor into a substantial J-shape, said shaping means including a substantially linear proximal portion, a terminal portion terminating adjacent to said distal electrode tip, and a curvilinear portion between said linear and terminal portions, said distal electrode tip being positioned adjacent to said linear portion.

3. An atrial electrode lead according to claim 2 wherein said shaping means comprises a shaped sheath of resilient material encasing a portion of said first pliant insulating tube surrounding said first conductor adjacent to said distal end of said first conductor.

4. An atrial electrode lead according to claim 3 wherein said curvilinear portion is arcuate and has an inside radius in the range of 3 mm to 8 mm, measured from the center of curvature to the innermost face of the outer surface of said curvilinear portion.

5. An atrial electrode lead according to claim 4 wherein said terminal portion has a length such that the furthermost distance from the exposed surface of said distal electrode tip to the innermost face of said curvilinear portion is in the range of 10 mm to 28 mm.

6. An atrial electrode lead according to claim 5 wherein said distal electrode tip is positioned in a range of 5 mm to 15 mm from the outer surface of said linear proximal portion when said J-shaped portion of said lead is in a relaxed position.

7. An atrial electrode lead according to claim 5 wherein said distal electrode tip is positioned in a range of zero to 5 mm from the outer surface of said linear proximal portion when said J-shaped portion of the lead is in a relaxed position.

8. An atrial electrode lead according to claim 5 wherein said distal electrode tip overlaps said linear proximal portion when said J-shaped portion of the lead is in a relaxed position.

9. An atrial electrode lead according to claim 4 wherein said distal electrode tip is positioned in a range of 5 mm to 15 mm from the outer surface of said linear proximal portion when said J-shaped portion of said lead is in a relaxed position.

10. An atrial electrode lead according to claim 4 wherein said distal electrode tip is positioned in a range of zero to 5 mm from the outer surface of said linear proximal portion when said J-shaped portion of the lead is in a relaxed position.

11. An atrial electrode lead according to claim 4 wherein said distal electrode tip overlaps said linear proximal portion when said J-shaped portion of the lead is in a relaxed position.

12. An atrial electrode lead according to claim 3 wherein said terminal portion has a length such that the furthermost distance from the exposed surface of said distal electrode tip to the innermost face of said curvilinear portion is in the range of 10 mm to 28 mm.

13. An atrial electrode lead according to claim 12 wherein said distal electrode tip is positioned in a range of 5 mm to 15 mm from the outer surface of said linear proximal portion when said J-shaped portion of said lead is in a relaxed position.

14. An atrial electrode lead according to claim 12 wherein said distal electrode tip is positioned in a range of zero to 5 mm from the outer surface of said linear proximal portion when said J-shaped portion of the lead is in a relaxed position.

15. An atrial electrode lead according to claim 12 wherein said distal electrode tip overlaps said linear proximal portion when said J-shaped portion of the lead is in a relaxed position.

16. An atrial electrode lead according to claim 3 wherein said distal electrode tip is positioned in a range of 5 mm to 15 mm from the outer surface of said linear proximal portion when said J-shaped portion of said lead is in a relaxed position.

17. An atrial electrode lead according to claim 3 wherein said distal electrode tip is positioned in a range of zero to 5 mm from the outer surface of said linear proximal portion when said J-shaped portion of the lead is in a relaxed position.

18. An atrial elecrode lead according to claim 3 wherein said distal electrode tip overlaps said linear proximal portion when said J-shaped portion of the lead is in a relaxed position.

19. An atrial electrode lead according to claim 3 further including a plurality of non-conducting resilient tines extending angularly from said distal electrode tip, said tines having a length sufficient to engage the musculae pectinatae of the right atrial appendage of the heart to secure said electrode lead adjacent to said crista terminalis both when the heart is swollen and not swollen with blood.

20. An atrial electrode lead according to claim 19 wherein said plurality of tines includes a first tine shorter than at least one of the remaining tines.

21. An atrial electrode lead according to claim 20 wherein said first tine when folded proximally extends 4 mm to 6 mm from said electrode tip.

22. An atrial electrode lead according to claim 20 wherein at least one of said remaining tines, when folded proximally extends in a range from 8 mm to 12 mm from said electrode tip.

23. An atrial electrode lead according to claim 20 wherein said tines are formed of silicone elastomer material and said first pliant insulating tube is made of polyurethane.

24. An atrial electrode lead according to claim 2 wherein said curvilinear portion is arcuate and has an inside radius in the range of 3 mm to 8 mm, measured from the center of curvature to the innermost face of the outer surface of said curvlinear portion.

25. An atrial electrode lead according to claim 24 wherein said terminal portion has a length such that the furthermost distance from the exposed surface of said distal electrode tip to the innermost face of said curvilinear portion is in the range of 10 mm to 28 mm.

26. An atrial electrode lead according to claim 25 wherein said distal electrode tip is positioned in a range of 5 mm to 15 mm from the outer surface of said linear proximal portion when said J-shaped portion of said lead is in a relaxed position.

27. An atrial electrode lead according to claim 25 wherein said distal electrode tip is positioned in a range of zero to 5 mm from the outer surface of said linear proximal portion when said J-shaped portion of the lead is in a relaxed position.

28. An atrial electrode lead according to claim 25 wherein said distal electrode tip overlaps said linear proximal portion when said J-shaped portion of the lead is in a relaxed position.

29. An atrial electrode lead according to claim 24 wherein said distal electrode tip is positioned in a range of 5 mm to 15 mm from the outer surface of said linear proximal portion when said J-shaped portion of said lead is in a relaxed position.

30. An atrial electrode lead according to claim 24 wherein said distal electrode tip is positioned in a range of zero to 5 mm from the outer surface of said linear proximal portion when said J-shaped portion of the lead is in a relaxed position.

31. An atrial electrode lead according to claim 24 wherein said distal electrode tip overlaps said linear proximal portion when said J-shaped portion of the lead is in a relaxed position.

32. An atrial electrode lead according to claim 2 wherein said terminal portion has a length such that the furthermost distance from the exposed surface of said distal electrode tip to the innermost face of said curvilinear portion is in the range of 10 mm to 28 mm.

33. An atrial electrode lead according to claim 32 wherein said distal electrode tip is positioned in a range of 5 mm to 15 mm from the outer surface of said linear proximal portion when said J-shaped portion of said lead is in a relaxed position.

34. An atrial electrode lead according to claim 32 wherein said distal electrode tip is positioned in a range of zero to 5 mm from the outer surface of said linear proximal portion when said J-shaped portion of the lead is in a relaxed position.

35. An atrial electrode lead according to claim 32 wherein said distal electrode tip overlaps said linear proximal portion when said J-shaped portion of the lead is in a relaxed position.

36. An atrial electrode lead according to claim 2 wherein said distal electrode tip is positioned in a range of 5 mm to 15 mm from the outer surface of said linear portion when said J-shaped portion of said lead is in a relaxed position.

37. An atrial electrode lead according to claim 2 wherein said distal electrode tip is positioned in a range of zero to 5 mm from the outer surface of said linear proximal portion when said J-shaped portion of the lead is in a relaxed position.

38. An atrial electrode lead according to claim 2 wherein said distal electrode tip overlaps said linear proximal portion when said J-shaped portion of the lead is in a relaxed position.

39. An atrial electrode lead according to claim 2 further including a plurality of non-conducting resilient tines extending angularly from said distal electrode tip, said tines having a length sufficient to engage the musculae pectinatae of the right atrial appendage of the heart to secure said electrode lead adjacent to said crista terminalis both when the heart is swollen and not swollen with blood.

40. An atrial electrode lead according to claim 39 wherein said plurality of tines includes a first tine shorter than at least one of the remaining tines.

41. An atrial electrode lead according to claim 40 wherein said first tine when folded proximally extends 4 mm to 6 mm from said electrode tip.

42. An atrial electrode lead according to claim 40 wherein at least one of said remaining tines, when folded proximally extends in a range from 8 mm to 12 mm from said electrode tip.

43. An atrial electrode lead according to claim 40 wherein said tines are formed of silicone elastomer material and said first pliant insulating tube is made of polyurethane.

44. An atrial electrode lead according to claim 3 wherein said first pliant insulating tube is made of polyurethane and said sheath of resilient material comprises silicone elastomer material.

45. An atrial electrode lead according to claim 1 further including a plurality of non-conducting resilient tines extending angularly from said distal electrode tip, said tines having a length sufficient to engage the musculae pectinatae of the right atrial appendage of the heart to secure said electrode lead adjacent to said crista terminalis both when the heart is swollen and not swollen with blood.

46. An atrial electrode lead according to claim 45 wherein said plurality of tines includes a first tine shorter than at least one of the remaining tines.

47. An atrial electrode lead according to claim 46 wherein said first tine when folded proximally extends 4 mm to 6 mm from said electrode tip.

48. An atrial electrode lead according to claim 46 wherein at least one of said remaining tines when folded proximally extends in a range from 8 mm to 12 mm from said electrode tip.

49. An atrial electrode lead according to claim 46 wherein said tines are formed of silicone elastomer material and said first pliant insulating tube is made of polyurethane.

50. An atrial electrode lead according to claim 45 wherein said tines are formed of silicone elastomer material and said first pliant insulating tube is made of polyurethane.

51. An atrial electrode lead in accordance with claim 1 further including:
   a second conductor having a proximal end and a distal end, and being electrically insulated from said first conductor;
   a second pliant insulating tube surrounding said second conductor;
   a second electrode positioned proximally to said distal electrode tip, and electrically connected to said second conductor;
   a second coupling member electrically connected to said proximal end of said second conductor, and cooperating with said first coupling member for connecting said electrode lead to said cardiac pacemaker circuitry module.

52. A bipolar atrial electrode lead for connection to a cardiac pacemaker circuit module comprising:
   a first conductor having a proximal end and a distal end;
   a first pliant insulating tube surrounding said first conductor;
   a distal electrode tip electrically connected to said distal end of said first conductor;
   means for shaping said first conductor to bend around the crista terminalis of the heart to place a distal electrode tip into substantial electrical contact with the cardiac tissue at the junction between the superior margin of the right atrial appendage and the origin of the crista terminalis when said bipolar atrial electrode lead is inserted into the right atrium of a human heart;
   a second conductor having a proximal end and a distal end, and being electrically insulated from said first conductor;
   a second pliant insulating tube surrounding said second conductor;
   a second electrode positioned proximally to said distal electrode tip and electrically connected to said second conductor; and
   first and second coupling members electrically connected to said proximal end of said first and second conductors, respectively, and adapted for connection to said cardiac pacemaker circuit module.

53. An atrial electrode lead according to claim 52 wherein said shaping means further reinforces said first conductor proximally to said distal electrode tip to shape said first conductor into a substantial J-shape, said shaping means comprising a substantially linear proximal portion, a terminal portion terminating adjacent to said distal electrode tip, and a curvilinear portion between said linear proximal and terminal portions positioning said distal electrode tip adjacent to said linear proximal portion.

54. An atrial electrode lead according to claim 53 wherein said curvilinear portion is arcuate and has an inside radius in the range of 3 mm to 8 mm, measured from the centre of curvature to the innermost face of the outer surface of said curvilinear portion.

55. An atrial electrode lead according to claim 53 wherein said terminal portion has a length such that the furthermost distance from the exposed surface of said distal electrode tip to the innermost face of said curvilinear portion is in the range of 10 mm to 28 mm.

56. An atrial electrode lead according to claim 53 wherein said distal electrode tip is positioned in a range of 5 mm to 15 mm from the outer surface of said linear proximal portion when said J-shaped portion of said lead is in a relaxed position.

57. An atrial electrode lead according to claim 53 wherein said distal electrode tip is positioned in a range of zero to 5 mm from the outer surface of said linear proximal portion when said J-shaped portion of said lead is in a relaxed position.

58. An atrial electrode lead according to claim 53 wherein said distal electrode tip overlaps said linear proximal portion when said J-shaped portion of said lead is in a relaxed position.

59. An atrial electrode lead according to claim 53 further including a plurality of non-conducting resilient tines extending angularly from said distal electrode tip, said tines havng a length sufficient to engage the musculae pectinatae of the right atrial appendage of the heart to secure said electrode lead adjacent to said crista terminalis both when the heart is swollen and not swollen with blood.

60. An atrial electrode lead according to claim 59 wherein said plurality of tines includes a first tine shorter than at least one of the remaining tines.

61. An atrial electrode lead according to claim 60 wherein said first tine when folded proximally extends 4 mm to 6 mm from said electrode tip.

62. An atrial electrode lead according to claim 60 wherein at least one of said remaining tines, when folded proximally extends in a range from 8 mm to 12 mm from said electrode tip.

63. An atrial electrode lead according to claim 59 wherein said tines are formed of silicone elastomer material and said first pliant insulating tube is made of polyurethane.

64. A bipolar atrial electrode lead in accordance with claim 53 wherein said second electrode is positioned within said curvilinear portion.

65. An atrial electrode lead in accordance with claim 53 wherein said second electrode is proximal to said curvilinear portion and wherein said first and second electrodes are equidistant from the center of curvature of said curvilinear portion.

66. An atrial electrode lead according to claim 52 wherein said shaping means comprises a shaped sheath of resilient material encasing a portion of said first pliant insulating tube and said first conductor adjacent to said distal end of said first conductor.

67. An atrial electrode lead according to claim 66 wherein said first pliant insulating tube is made of polyurethane and said sheath of resilient material comprises silicone elastomer material.

68. An atrial electrode lead in accordance with claim 52 wherein said shaping means comprises a substantially J-shaped sleeve surrounding a portion of said second pliant insulating tube proximal to said distal electrode tip.

69. An atrial electrode lead in accordance with claim 52 wherein said second electrode comprises an uninsulated portion of said second conductor.

* * * * *